US00PP24736P2

(12) United States Plant Patent
Hanes

(10) Patent No.: US PP24,736 P2
(45) Date of Patent: Aug. 5, 2014

(54) ***PELARGONIUM* PLANT NAMED 'PEQZ0003'**

(50) Latin Name: ***Pelargonium* spp.**
Varietal Denomination: PEQZ0003

(75) Inventor: Mitchell Hanes, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 91 days.

(21) Appl. No.: 13/507,803

(22) Filed: Jul. 30, 2012

(51) Int. Cl.
*A01H 5/00* (2006.01)

(52) U.S. Cl.
USPC ..... Plt./324

(58) Field of Classification Search
USPC ..... Plt./324, 329, 330
See application file for complete search history.

*Primary Examiner* — Susan McCormick Ewoldt
(74) *Attorney, Agent, or Firm* — Joshua L. Price

(57) ABSTRACT

A new *Pelargonium* plant named 'PEQZ0003' particularly distinguished by the bright red-purple colored inflorescences held above the medium-green foliage, very heat and drought tolerant with continuous color through the most extreme summer heat, and exceptional edema tolerance on a well-branched plant habit.

1 Drawing Sheet

Latin name of the genus and species of the plant claimed: *Pelargonium* spp.
Varietal denomination: 'PEQZ0003'.

BACKGROUND OF THE NEW PLANT

The present invention comprises a new *Pelargonium*, botanically known as *Pelargonium* L'Hérit. Ex Aiton, and hereinafter referred to by the variety name 'PEQZ0003'.

'PEQZ0003' is a product of a planned breeding program. The new cultivar 'PEQZ0003' has bright red-purple colored inflorescences held above the medium-green foliage, very heat and drought tolerant with continuous color through the most extreme summer heat, and exceptional edema tolerance on a well-branched plant habit.

'PEQZ0003' originates from a hybridization in a controlled breeding program made in February 2007, in a greenhouse in Gilroy, Calif. The female parent of 'PEQZ0003' was an unpatented, proprietary plant of inter-specific origin, derived from crosses between *Pelargonium×hortorum, Pelargonium peltatum* and *Pelargonium tongaense* lines, and identified as '10521-1' with a lighter rose color florets and a smaller more open plant habit when compared to 'PEQZ0003'.

The male parent of 'PEQZ0003' was an unpatented, proprietary plant of inter-specific parentage, derived from crosses between *Pelargonium×hortorum, Pelargonium peltatum* and *Pelargonium tongaense* lines, and identified as '10520-1' with more blue-rose colored florets and a more open plant habit when compared to 'PEQZ0003'. The resultant seed was sown in August 2007.

'PEQZ0003' was selected as one flowering plant within the progeny of the stated cross in December 2007 in a greenhouse in Gilroy, Calif.

The first act of asexual reproduction of 'PEQZ0003' was accomplished when vegetative cuttings were propagated from the initial selection in the December 2007 in a greenhouse in Gilroy, Calif.

BRIEF SUMMARY OF INVENTION

Horticultural examination of plants grown from cuttings of the plant initiated in December 2007 in Gilroy, Calif., and continuing thereafter, has demonstrated that the combination of characteristics as herein disclosed for 'PEQZ0003' are firmly fixed and are retained through successive generations of asexual reproduction.

'PEQZ0003' has not been observed under all possible environmental conditions. The phenotype may vary significantly with variations in environment such as temperature, light intensity, and day length.

A Plant Breeder's Right for this cultivar was applied for in Canada on Nov. 1, 2011, No. 11-7414. 'PEQZ0003' has not been made publicly available more than one year prior to the filing of this application.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

The accompanying photographic drawing shows typical flower and foliage characteristics of 'PEQZ0003' with colors being as true as possible with an illustration of this type.

Figure 1:
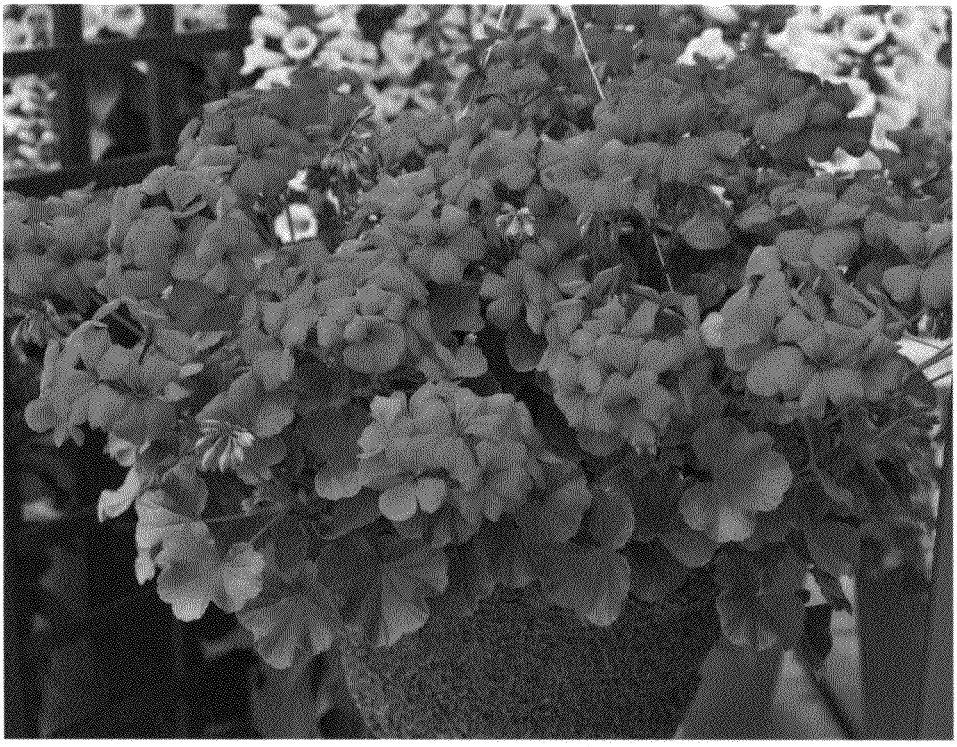
Figure 2:
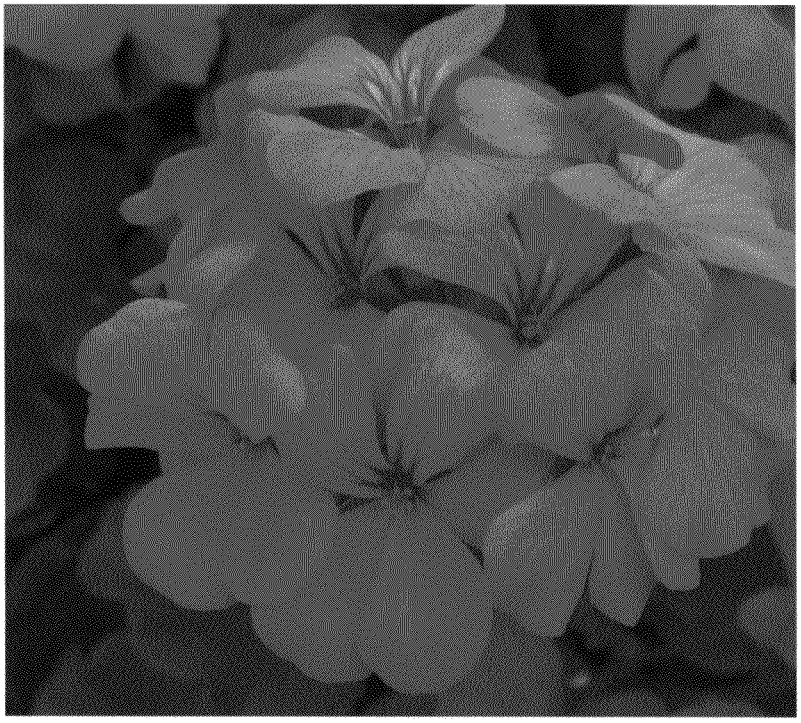

The photographic drawing shows in FIG. 1, 3 flowering plants of the new variety and in FIG. 2, a close-up of an inflorescence.

DETAILED BOTANICAL DESCRIPTION

The plant descriptions and measurements were taken in Gilroy, Calif. in late May 2012 under natural light. These plants were approximately 17-19 weeks old and were grown in a 1 gallon pots, in a greenhouse trial. The plants shown in the photographs were about 25 weeks old growing in a 10 inch pot in a greenhouse. The photographs were taken in April 2012.

Color references are made to The Royal Horticultural Society Colour Chart (R.H.S.) 2001.

TABLE 1

DIFFERENCES BETWEEN THE NEW VARIETY 'PEQZ0003' AND A MOST SIMILAR VARIETY

| | 'PEQZ0003' | 'Cante Ros' (U.S. Plant Pat. No. 15,834) |
|---|---|---|
| Floret size: | Larger | Smaller |
| Floret petal color: | Deeper | Lighter |
| Umbel diameter size: | Larger | Smaller |
| Peduncle length: | Shorter | Longer |

Plant:

*Form, growth and habit.*—Upright, outwardly spreading and rounded growth habit, heat and drought tolerant with continuous color through the most extreme summer heat, edema tolerance, well-branched plant habit.

*Plant height.*—16-18.0 cm.

*Plant height (inflorescence included).*—20-23.0 cm.

*Plant width.*—34-37.0 cm.

Roots:

*Number of days to initiate roots.*—15-18 days at about 22 degrees C.

*Number of days to produce a rooted cutting.*—21-23 days at 22 degrees C.

*Type.*—Fine, fibrous, free branching.

*Color.*—RHS N155B but whiter.

Foliage:

*Immature leaf, color upper surface.*—Closest to RHS 137A with a slightly lighter mottling.

*Immature leaf, lower surface.*—Closest to RHS 137C.

*Mature leaf, color upper surface.*—Closest to RHS 137A with slightly lighter mottling.

*Mature leaf, color lower surface.*—Closest to RHS 137C.

*Length.*—4.3-4.6 cm.

*Width.*—7.5-7.9 cm.

*Shape.*—Cordate.

*Base shape.*—Cordate.

*Apex shape.*—Acute.

*Margin.*—Slightly dentate.

*Texture upper side.*—Hirsute.

*Texture lower side.*—Hirsute.

*Leaf zonation color.*—None.

*Color of veins, upper surface.*—RHS 137C becoming indistinct.

*Color of veins, lower surface.*—RHS 137C becoming indistinct.

*Pattern of veining.*—Palmate.

*Petiole color.*—RHS 137C.

*Petiole length.*—6-9.0 cm.

*Diameter of petiole.*—0.2 cm.

*Texture.*—Pilose, hirsute, glandular hairs.

Stem:

*Quantity of branches.*—8-10.

*Color of stem.*—Between RHS 144A and RHS 144B.

*Length of stem.*—10-12.0 cm.

*Diameter.*—0.5 cm.

*Length of internodes.*—1.5 cm.

*Texture.*—Sparsely hirsute, pilose, glandular hairs.

Peduncle:

*Color of peduncle.*—RHS 137C.

*Length of peduncle.*—13-15.0 cm.

*Peduncle diameter.*—0.3-0.35 cm.

*Texture.*—Hirsute, glandular hairs.

Pedicel:

*Color of pedicel.*—Between RHS 187A and RHS 166A.

*Length of pedicel.*—3.2-3.6 cm.

*Diameter of pedicel.*—0.15-0.2 cm.

*Texture.*—Sparsely pilose, glandular hiars.

Bud (just before opening):

*Color.*—Closest to RHS N57A with more red.

*Length.*—1.5 cm.

*Width.*—0.7-0.8 cm.

*Shape.*—Elliptical.

Inflorescence:

*Type.*—Umbel; semi-spherical or nearly semi-spherical.

*Lastingness of individual flowers.*—7-9 days at 18° C. temperature.

*Number of inflorescences per plant.*—12.

*Number of flowers per inflorescence.*—Approximately 13-20.

*Fragrance.*—None.

*Umbel diameter.*—12-14.0 cm.

*Umbel depth.*—6.5-7.5 cm.

Corolla:

*Form.*—Single.

*Number of petals.*—5.

*Diameter of flower.*—About 5.0 cm.

*Depth of flower.*—2-2.5 cm.

*Color upper petals, upper surface.*—Closest to RHS N57A but brighter and deeper, with RHS 53B veining.

*Color upper petals, lower surface.*—Closest to RHS 58B.

*Length of upper petals.*—3.0 cm.

*Width of upper petals.*—1.9 cm.

*Color lower petals, upper surface.*—Closest to RHS N57A but brighter and deeper.

*Color lower petals, lower surface.*—Closest to RHS 58B.

*Length of lower petals.*—2.7 cm.

*Width of lower petals.*—2.2 cm.

*Petal shape.*—Obovate to spathulate.

*Apex shape.*—Rounded.

*Margin.*—Entire.

*Base.*—Attenuate.

*Petal texture.*—Papillose on both surfaces.

Calyx:

*Number of sepals.*—5.

*Color of sepals.*—RHS 144A mottled with anthcyanins of about RHS 178B.

*Length of sepals.*—1.2 cm.

*Width of sepals.*—0.3-0.4 cm.

*Sepal shape.*—Lanceolate to linear.

*Apex shape.*—Acute.

*Margins.*—Mostly fused.

*Texture, upper surface.*—Glabrous.

*Lower surface.*—Glandular hairs, hirsute.

Reproductive organs:

Gynoecium:

*Pistil.*—1.

*Length.*—1.1 cm.

*Style color.*—Closest to RHS 53D.

*Style length.*—0.6-0.7 cm.

*Stigma color.*—Closest to RHS 53D.

*Ovary color.*—Between RHS 144A and RHS 144B.

*Ovary length.*—0.4-0.5 cm.

*Ovary diameter.*—0.2 cm.

Androecium:

*Number of stamens*.—7.

*Color of filaments*.—RHS N57B with RHS N155C basally.

*Length filaments*.—0.7 cm.

*Anther color*.—Between RHS 25B and RHS 25C with a light mottling of RHS N57B.

*Length of anthers*.—0.2 cm.

*Color of pollen*.—RHS 25B.

*Pollen amount*.—Normal.

*Fertility/seed set*.—Has not been determined to date.

*Disease/pest resistance*.—Has not been determined to date.

What is claimed is:

1. A new and distinct variety of *Pelargonium* plant named 'PEQZ0003' substantially as illustrated and described herein.

* * * * *